US00PP35487P2

(12) United States Plant Patent
Serrato

(10) Patent No.: US PP35,487 P2
(45) Date of Patent: Nov. 21, 2023

(54) PSIDIUM TREE NAMED 'SERRATO 13'

(50) Latin Name: *Psidium guajava*
Varietal Denomination: SERRATO 13

(71) Applicant: Jaime Serrato, Valley Center, CA (US)

(72) Inventor: Jaime Serrato, Valley Center, CA (US)

( * ) Notice: Subject to any disclaimer, the term of this patent is extended or adjusted under 35 U.S.C. 154(b) by 0 days.

(21) Appl. No.: 18/445,017

(22) Filed: Mar. 2, 2023

(51) Int. Cl.
*A01H 5/08* (2018.01)
*A01H 6/00* (2018.01)

(52) U.S. Cl.
USPC ..... Plt./156

(58) Field of Classification Search
USPC ..... Plt./156
See application file for complete search history.

*Primary Examiner* — Susan McCormick Ewoldt
(74) *Attorney, Agent, or Firm* — Samuel R. McCoy, Jr.

(57) ABSTRACT

A new and distinct *Psidium* tree named 'SERRATO 13' which is characterized by the combination of a globular growth habit of the canopy, early-season fruiting, moderately high fruit yield, large pyriform-shaped fruit with fewer seeds and dense, firm flesh with a sweet flavor, and the stability of these characteristics from generation to generation.

3 Drawing Sheets

Latin name of the genus and species: The Latin name of the genus and species of the novel variety disclosed herein is *Psidium guajava.*

Variety denomination: The inventive cultivar of *Psidium* disclosed herein has been given the variety denomination 'SERRATO 13'.

BACKGROUND OF THE INVENTION

Parentage: 'SERRATO 13' originated as a seedling selection from the open pollination of a plurality of *Psidium guajava* 'SERRATO 3' (unpatented) trees, a variety developed and owned by the inventor, at his exotic fruit farm in Valley Center, California. The pollen parent is presumed to also be 'SERRATO 3', given the fact that there were no other cultivars in close proximity to the seed parent.

In the course of normal operations, the inventor will initiate cultivation of a new *Psidium guajava* orchard by first grafting scions of the variety to be produced in the new orchard onto vigorous rootstock. To produce said scions, seeds are harvested from the variety to be produced in the new orchard, germinated in propagation trays, and subsequently grown in nursery containers. Scions are then harvested from these juvenile trees and grafted to the desired rootstock. The newly grafted trees are then grown in 5-gallon nursery containers before being transplanted to the field for commercial fruit production.

The claimed plant originated from this same process. Seeds were harvested from a plurality of 'SERRATO 3' trees and the resulting seedlings were later used to establish a new orchard. In 2014, over the course of the fruiting period, the inventor observed 29 trees which were phenotypically different from the parent. These 29 trees exhibited variations in growth habit and fruiting. The claimed tree was observed to fruit earlier and yield more fruit than the parent plants. After further evaluation to confirm the uniqueness and stability of the characteristics first observed, the claimed plant was selected for commercial production and was given the name 'SERRATO 12'.

Asexual Reproduction: Asexual reproduction of 'SERRATO 13', by way of grafting, was first performed in 2014 in Valley Center, California. Through one subsequent generation, the unique features of this cultivar have proven to be stable and true to type.

SUMMARY OF THE INVENTION

The cultivar 'SERRATO 13' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SERRATO 13'. These characteristics in combination distinguish 'SERRATO 13' as a new and distinct *Psidium guajava* cultivar:

1. 'SERRATO 13' exhibits a freely-branching and densely-foliaged growth habit with a globular tree crown; and
2. *Psidium* 'SERRATO 13' exhibits early-season fruiting with a fruiting period of approximately three months; and
3. *Psidium* 'SERRATO 13' exhibits large, pyriform-shaped fruit with a relatively low quantity of seeds; and
4. *Psidium* 'SERRATO 13' exhibits aromatic fruit with dense, moderately firm flesh and a sweet flavor; and
5. *Psidium* 'SERRATO 13' exhibits a moderately high fruit yield, with each tree producing approximately 90 kilograms of fruit per harvest season.

BOTANICAL DESCRIPTION OF THE PLANT

Figure 1:
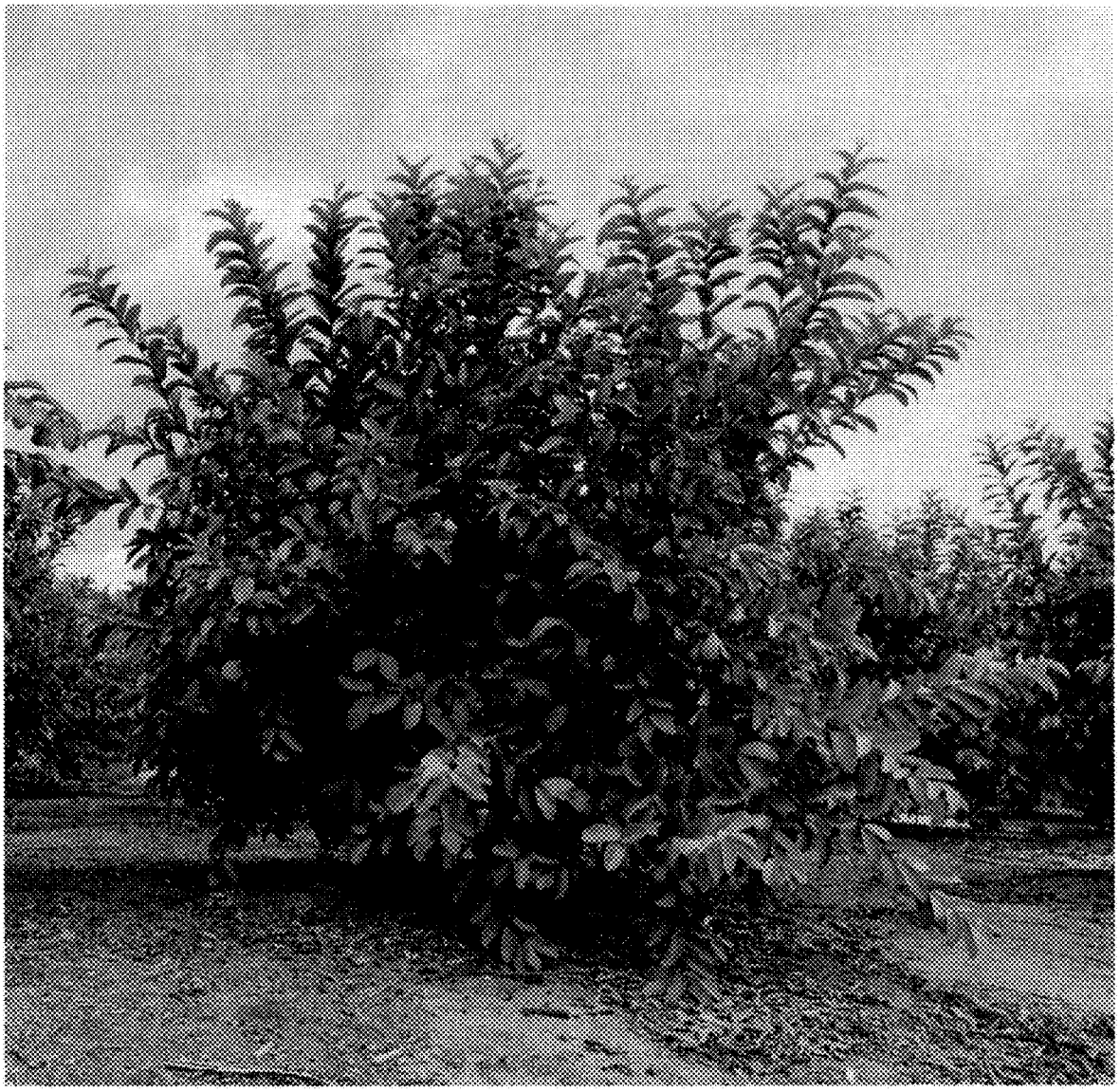
FIG. 1 illustrates, as nearly true as it is reasonably possible to make the same in color photographs of this type, an exemplary 4-year-old field-grown 'SERRATO 13' tree in Valley Center, California.
Figure 2:
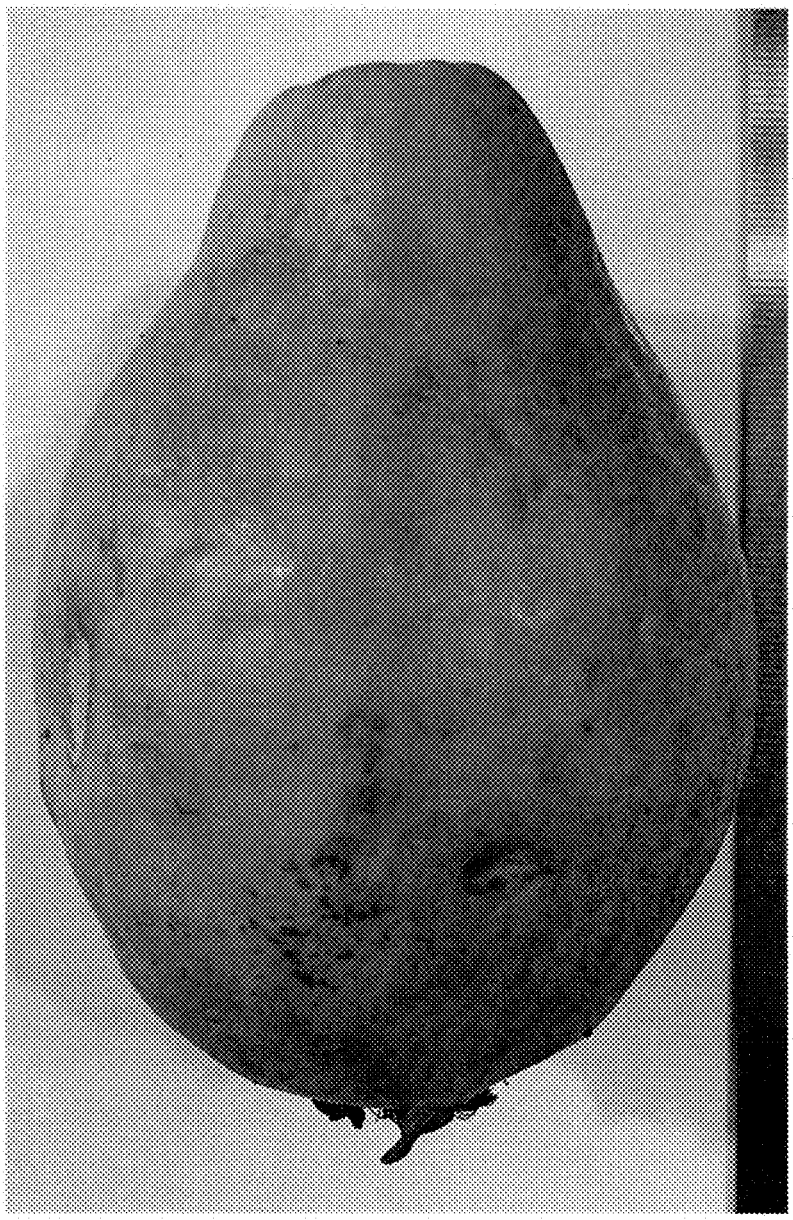
FIG. 2 illustrates, as nearly true as it is reasonably possible to make the same in color photographs of this type, the fruit of 'SERRATO 13'.
Figure 3:
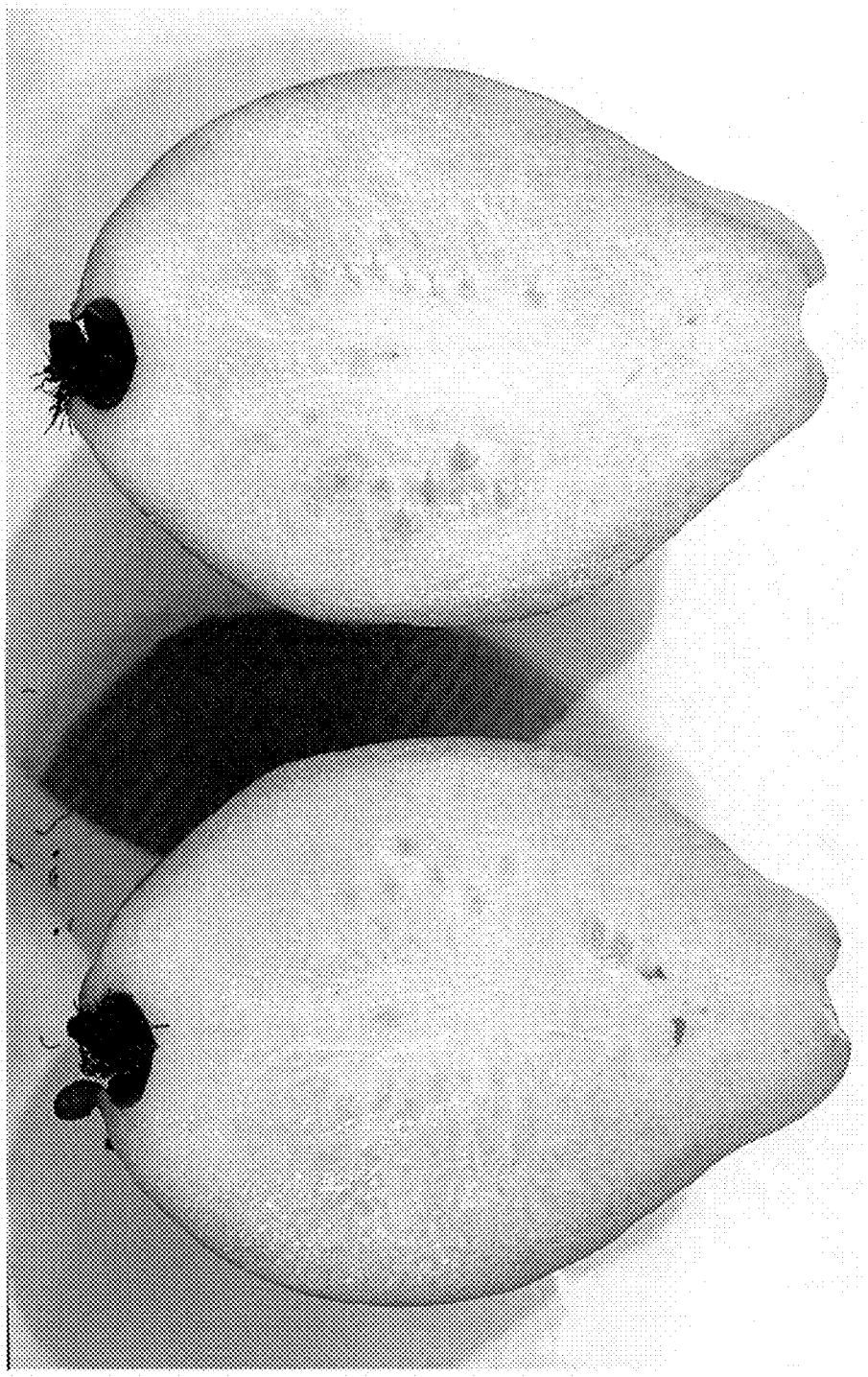
FIG. 3 illustrates, as nearly true as it is reasonably possible to make the same in color photographs of this type, a cross section of the mature fruit of 'SERRATO 13'.

The following observations and measurements were made in December of 2021 and describe a 4 year old grafted, field-grown 'SERRATO 13' tree on *Psidium guajava* '300' rootstock, grown plant in Valley Center, California. The tree was grown in full sun, regularly irrigated with low-volume overhead irrigation, and fertigated with a high Potassium and Calcium fertilizer approximately 3 to 4 times a year beginning when fruiting is initiated. Except for the application of a preventative biological fungicide, no chemical treatments of any kind were utilized. Trees are pruned once a year, after harvesting has concluded.

Those skilled in the art will appreciate that certain characteristics will vary with older or, conversely, with younger plants. 'SERRATO 13' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 1986 edition.

A botanical description of 'SERRATO 13' and comparisons with the parent plant and most similar commercial *Psidium* cultivar known to the inventor are provided below.

Plant description:

*Growth habit*.—Small, evergreen, fruit-bearing tree.

*Crown profile*.—Globular.

*Average height from base to top of foliage*.—Approximately 6.0 to 7.25 m.

*Average width*.—Approximately 4.25 m to 5.0 m.

*Plant vigor*.—Moderately vigorous.

*Propagation details*.—Asexual propagation is accomplished by grafting a scion onto rootstock. The most commonly used rootstock is '300', a variety developed and owned by the inventor. Scions form a union with the rootstock in approximately 3 to 4 weeks.

*Time to produce a fruit-bearing tree*.—Approximately 1 to 2 years from planting of a grafted tree into the orchard.

*Disease and pest resistance or susceptibility*.—Neither tolerance nor resistance to normal diseases and pests of *Psidium guajava* have been observed.

*Environmental tolerances*.—Hardy to USDA Zone 9; heat and drought tolerant once established.

Root system:

*General*.—Extensive, freely-branching, shallow, and generally extending beyond the tree canopy; some deeper roots but no taproot.

Stems:

*Branching habit*.—Single rootstock leader gives rise to an abundance of lateral branches above the graft union.

*Attitude*.—Upward and outward to pendulous, as branches age.

*Aspect*.—Quadrangular.

*Length of lateral branches*.—119 cm.

*Diameter of fruiting branches*.—Averaging 1.25 cm at the base.

*Internode length on lateral branches*.—7.5 cm on average.

*Texture*.—Juvenile branches are smooth and moderately tomentose and become progressively fibrous and fissured as they age; branches will exfoliate as wood matures, revealing a smooth texture beneath.

*Strength*.—Moderately strong and pliable.

*Color, juvenile*.—Youngest wood is yellow-green, RHS 145A and suffused with RHS 151A; as wood matures it becomes colored with a mixture of greyed-orange and grey-brown, RHS 177A and 199A, and is heavily suffused with greyed-orange, nearest to in between RHS 166A and 175B.

*Color, mature*.—Greyed-orange, nearest to a combination of RHS 165A, 165B, 166C, and 174A; exfoliated fibers are grey-brown, nearest to a combination of RHS 199A, 199B, and 200C but predominantly 199B and 200C.

*Pubescence*.—Juvenile branches are moderately tomentose; mature branches are glabrous.

Foliage:

*Arrangement*.—Opposite; decussate.

*Attachment*.—Petiolate.

*Division*.—Simple.

*Lamina*.—Dimensions — 17.6 cm long and 7.3 cm wide. Shape — Elliptic to obtuse or oblong. Aspect — Carinate and somewhat reflexed. Apex — Obtuse. Base — Obtuse. Margin — Entire with light, coarse undulation. Pubescence, adaxial surface — Glabrous. Texture and luster of adaxial surface — Somewhat bullate and moderately glossy. Pubescence, abaxial surface — Glabrous. Texture and luster of abaxial surface — Somewhat bullate and matte. Color — Juvenile foliage, adaxial surface — Nearest to in between green and yellow-green, RHS 137D and 144A; suffused with greyed-orange, nearest to a combination of RHS 164A and 175C. Juvenile foliage, abaxial surface — Yellow-green, RHS 145A. Mature foliage, adaxial surface — Nearest to in between green and yellow-green, RHS 137C and 147A. Mature foliage, abaxial surface — Yellow-green, nearest to in between RHS 146B and 147C. Venation — Pattern — Reticulate; prominently-veined. Color, adaxial surface — Yellow-green, nearest to a mixture of RHS 148B and 146B. Color, abaxial surface — Yellow-green, nearest to a mixture of RHS 151A and 152D.

*Petiole*.—Length — 12.3 mm. Width — 4.3 mm. Texture — Smooth and moderately tomentose. Strength — Strong. Color, adaxial surface — Yellow-green, nearest to a mixture of RHS 148B and 146B. Color, abaxial surface — Yellow-green, nearest to a mixture of RHS 151A and 152D.

Inflorescence:

*Type*.—No inflorescence; flowers are solitary, occurring individually or in small clusters in leaf axils.

Flower buds:

*Bud shape*.—Ovoid.

*Bud dimensions*.—Approximately 15 to 18 mm long and 10 to 12 mm in diameter.

*Bud color*.—Nearest to in between green and yellow-green, RHS 143C and 144A.

Flower:

*Bloom period*.—May through June.

*Flower type*.—Perfect; simple.

*Flower shape*.—Rotate.

*Persistence*.—Not persistent.

*Flower aspect*.—Upward and outward.

*Fragrance*.—Light fragrance.

*Dimensions*.—Approximately 2.5 cm in diameter and 2.0 cm deep.

*Pedicels*.—Dimensions — 10 to 20 mm long and 2.0 mm in diameter. Color — Nearest to in between green and yellow-green, RHS 143C and 144A. Texture and luster — Smooth, lightly tomentose, and matte. Strength — Low.

*Calyx*.—Arrangement — Irregularly rotate with sepals fused at the base, forming a short calyx tube. Dimensions — Approximately 14 to 16 mm long, including the calyx tube, and 8 to 11 mm wide at the widest point between outstretched lobes. Sepals — Quantity — Varying from 2 to 5 lobes. Fused or free — Fused. Sepal lobe dimensions — Approximately 8 to 10 mm long and varying from 6 to 8 mm wide. Sepal lobe shape — Broad elliptic. Sepal lobe apex — Broadly acute to near-obtuse. Aspect — Concave and becoming reflexed at anthesis. Margin — Entire; no undulation. Texture — Smooth and glabrous. Color — Nearest to in between green and yellow-green, RHS 143C and 144A.

*Petals*.—Arrangement — Rotate; petals arranged in a single whorl. Quantity — Typically 4 or 5. Fused or free — Free. Dimensions — Approximately 10 to 15 mm long and 10 to 11 mm wide. Shape — Broad elliptic. Apex — Broadly acute to near-obtuse. Base — Broadly cuneate. Aspect — Concave and becoming reflexed at anthesis. Margin — Entire; light, coarse undulation. Texture — Glabrous. Color — When opening, inner surface — White, RHS 155A. When opening, outer surface — White, RHS 155A. Inner surface, at anthesis — White, RHS 155A. Outer surface, at anthesis — White, RHS 155A. Color fading to — Not fading.

Reproductive organs:

*Androecium*.—Stamen quantity — Very abundant; more than 200. Filament — Dimensions — Approximately 10 to 12 mm long and approximately 0.75 mm in diameter. Color — White, RHS 155A; suffused with green-yellow towards the base, nearest to RHS 1D. Anther — Anther attachment — Dorsifixed. Anther shape — Oblong; dehiscing longitudinally. Anther size — 3.0 mm long and 1.5 mm in diameter. Anther color — White, RHS 155D, and lightly suffused with yellow-white at anthesis, nearest to RHS 158B. Pollen — Amount of pollen — Abundant. Pollen color — Yellow, RHS 10D.

*Gynoecium*.—Pistil quantity — One. Stigma — Shape — Round. Dimensions — Approximately 1.75 mm across and 2.0 mm tall. Color — Yellow-green, RHS 145B. Style — Dimensions — Approximately 10 to 12 mm long and 2.0 to 2.25 mm in diameter at the base. Color — Green-white, RHS 157D, and becoming suffused with yellow-green, RHS 145B towards the stigma. Ovary — Position — Inferior. Shape — Globose. Diameter — 10 to 12 mm.

Seed and fruit:

*Fruit*.—Type — Multi-seeded berry. Shape — Varying from pyriform to somewhat rounded, with a small calyx cavity and floral remnants present at the base. Dimensions — 6.7 cm in diameter and 8.6 cm long. Weight — 187 grams, on average. Texture — Somewhat smooth to slightly rough or bumpy. Aroma — Moderately to strongly fragrant with the strong, sweet, musky, tropical fruit scent. Flavor — Sweet, fruity, and slightly floral. Color — Epicarp — Immature fruit is yellow-green, nearest to a mixture of RHS 144A, 144B, 145A, 145B, and 145C; as fruit matures, it becomes progressively suffused with a combination of yellow and yellow-green (nearest to RHS 4B, 5C, and 151D) beginning near the calyx cavity and spreading proximally; once ripe, the entire epicarp is a combination of yellow and yellow-green nearest to RHS 4B, 5C, 151D, and 154C. Mesocarp — Yellow-green near the epicarp, a mixture of RHS 144C and 145A, and becoming a lighter shade of yellow-green towards the endocarp, nearest to a combination of RHS 145C and 145D. Endocarp — White, nearest to RHS 155A, and lightly suffused with orange-white, nearest to RHS 159B. Harvest season — October through December in Valley Center, California. Productivity of the fruit — A mature tree will produce approximately 90 kilograms of fruit per harvest season. Storage characteristics — Fruit stored for 12 to 15 days at 10 to 12 degrees Celsius show no signs of internal breakdown or ripening.

*Seed*.—Abundance — Seeds are embedded in the endocarp. Relatively fewer seeds than the parent and other known varieties approximately 125 to 150 seeds as observed. Shape — Irregularly globular. Size — 3.5 to 4.0 mm long and 4.0 mm in diameter. Color — Greyed-orange, nearest to in between RHS 163B and 163C. Texture and luster — Smooth and matte.

COMPARISON WITH THE PARENT PLANTS

Plants of the new cultivar 'SERRATO 13' may be distinguished from the parent, *Psidium* 'SERRATO 3' (not patented), by the characteristics described in Table 1.

TABLE 1

| Characteristic | 'SERRATO 13' | 'SERRATO 3' |
|---|---|---|
| Time to fruit. | Earlier than 'SERRATO 3'. | Later than 'SERRATO 13'. |
| Fruit yield. | 90 kilograms of fruit per tree, per season. | 70 kilograms of fruit per tree, per season. |
| Fruit firmness. | Firmer than 'SERRATO 3'. | Softer than 'SERRATO 13'. |
| Flavor of the fruit. | Sweeter than 'SERRATO 3'. | Less sweet, compared to SERRATO 13'. |

COMPARISON WITH THE CLOSEST KNOWN COMMERCIAL VARIETY

Plants of the new cultivar 'SERRATO 13' may be distinguished from the commercial variety, *Psidium* 'SERRATO 12' (U.S. Plant patent application Ser. No. 18/445,013 has been filed concurrently), by the characteristics described in Table 2.

TABLE 2

| Characteristic | 'SERRATO 13' | 'SERRATO 12' |
|---|---|---|
| Time to fruit. | Earlier than 'SERRATO 12'. | Later than 'SERRATO 13'. |
| Fruit size. | Larger than 'SERRATO 12'. | Smaller than 'SERRATO 13'. |
| Fruit firmness. | Softer than 'SERRATO 12'. | Firmer than 'SERRATO 13'. |
| Fruit aroma. | More aromatic than 'SERRATO 12'. | Less aromatic than 'SERRATO 13'. |

TABLE 2-continued

| Characteristic | 'SERRATO 13' | 'SERRATO 12' |
|---|---|---|
| Fruit yield. | 90 kilograms of fruit per tree, per season. | 115 kilograms of fruit per tree, per season. |

That which is claimed is:

1. A new and distinct cultivar of *Psidium* tree named 'SERRATO 13', substantially as described and illustrated herein.

* * * * *